Figure 1:
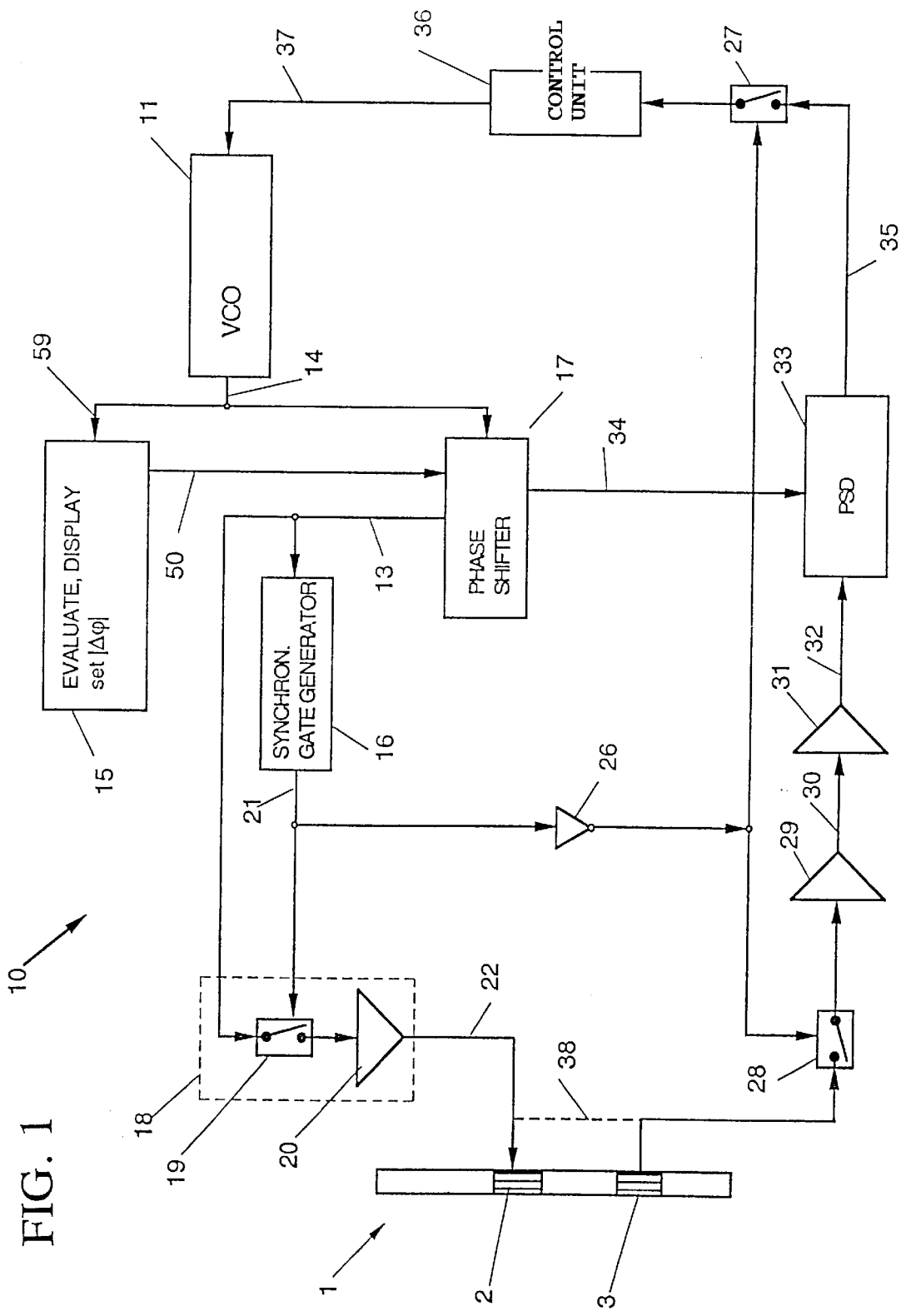

United States Patent

Goodbread et al.

[11] Patent Number: 5,837,885
[45] Date of Patent: Nov. 17, 1998

[54] METHOD AND DEVICE FOR MEASURING THE CHARACTERISTICS OF AN OSCILLATING SYSTEM

[76] Inventors: Joseph Goodbread, 1020 SW. Broadway Dr., Portland, Oreg. 97201; Mahir Sayir, Im Straler 7, 8047 Zurich, Switzerland; Klaus Hausler, Zurichstrasse 101, 8700 Kusnacht, Switzerland; Jurg Dual, Waldegg 10a, 8126 Zumikon, Switzerland

[21] Appl. No.: 605,203
[22] PCT Filed: Mar. 2, 1995
[86] PCT No.: PCT/EP95/00761
§ 371 Date: Aug. 29, 1996
§ 102(e) Date: Aug. 29, 1996
[87] PCT Pub. No.: WO95/24630
PCT Pub. Date: Sep. 14, 1995

[30] Foreign Application Priority Data

Mar. 7, 1994 [CH] Switzerland ................... 657/94

[51] Int. Cl.⁶ .............. G01N 9/32; G01N 29/02; G01N 29/24
[52] U.S. Cl. .............. 73/32 A; 73/54.26; 73/54.27; 73/54.41; 73/61.79; 73/64.42; 73/64.53; 73/861.355; 73/DIG. 1; 310/316; 310/338
[58] Field of Search .............. 73/32 A, 54.25, 73/54.26, 54.24, 54.27, 54.41, 61.79, 64.42, 64.53, 599, 702, 861.355, 861.357, 862.59, DIG. 1, 579; 310/338, 316; 331/107 A; 374/117

[56] References Cited

U.S. PATENT DOCUMENTS

| | | | |
|---|---|---|---|
| 3,712,117 | 1/1973 | Fitzgerald et al. | 73/59 |
| 4,023,400 | 5/1977 | November | 73/54 |
| 4,429,564 | 2/1984 | Ikeda et al. | 73/32 A |
| 4,566,181 | 1/1986 | Matusik et al. | 73/54 |
| 4,600,855 | 7/1986 | Strachan | 73/702 |
| 4,920,787 | 5/1990 | Dual et al. | 73/54 |
| 5,150,080 | 9/1992 | Bianchini et al. | 331/99 |
| 5,361,045 | 11/1994 | Beaussier et al. | 331/154 |

FOREIGN PATENT DOCUMENTS

| | | |
|---|---|---|
| 36 11 632 | 10/1986 | Germany. |
| 59-099332 | 6/1984 | Japan. |
| 60-194330 | 10/1985 | Japan. |
| 91/08447 | 6/1991 | WIPO. |

OTHER PUBLICATIONS

The Marconi Review, vol. 43, No. 218, 1980 Great Baddow, UK, pp. 156–175. R.M. Langdon, 'Vibratory process control transducer'.
J.Phys.E: Sci.Instrum., vol. 18, 1985 Bristol, UK, pp. 103–115. R.M. Langdon, 'Resonator sensors—a review'.
IEEE Transactions on Sonics and Ultrasonics, vol. 20, No. 4, Oct. 1973, New York, USA, pp. 340–346. R. Bruce Thompson, 'A model for the electromagnetic generation and detection of Rayleigh and Lamb waves'.

*Primary Examiner*—Hezron E. Williams
*Assistant Examiner*—Rose M. Miller
*Attorney, Agent, or Firm*—Browdy and Neimark

[57] ABSTRACT

A resonator (1) is vibrating close to its resonance frequency. The vibration is excited by one or a first transducer (2) connected to an oscillator (11). The vibration is measured by the transducer (2) or a second transducer (3) and stabilized by a phase-locked feedback loop comprising a phase sensitive detector (33), a feedback controller (36), a phase shifter (17) and means (15) to evaluate the measured frequencies. In order to measure the damping of the resonator (1), the phase in the phase shifter (17) is alternately set to two different values. The difference between the frequencies corresponding to these two phase values is a measure for the damping of the system. One or more switches (19, 28, 27) and a gate generator (16) make sure that excitation and measurement do not occur at the same time. Thereby, any cross-talk between driving and sensing transducers is completely eliminated. Also, a single transducer can be used to both excite and measure the vibration. Thereby, a very compact transducer set-up can be implemented and the precision and range of the measurement is improved.

17 Claims, 12 Drawing Sheets

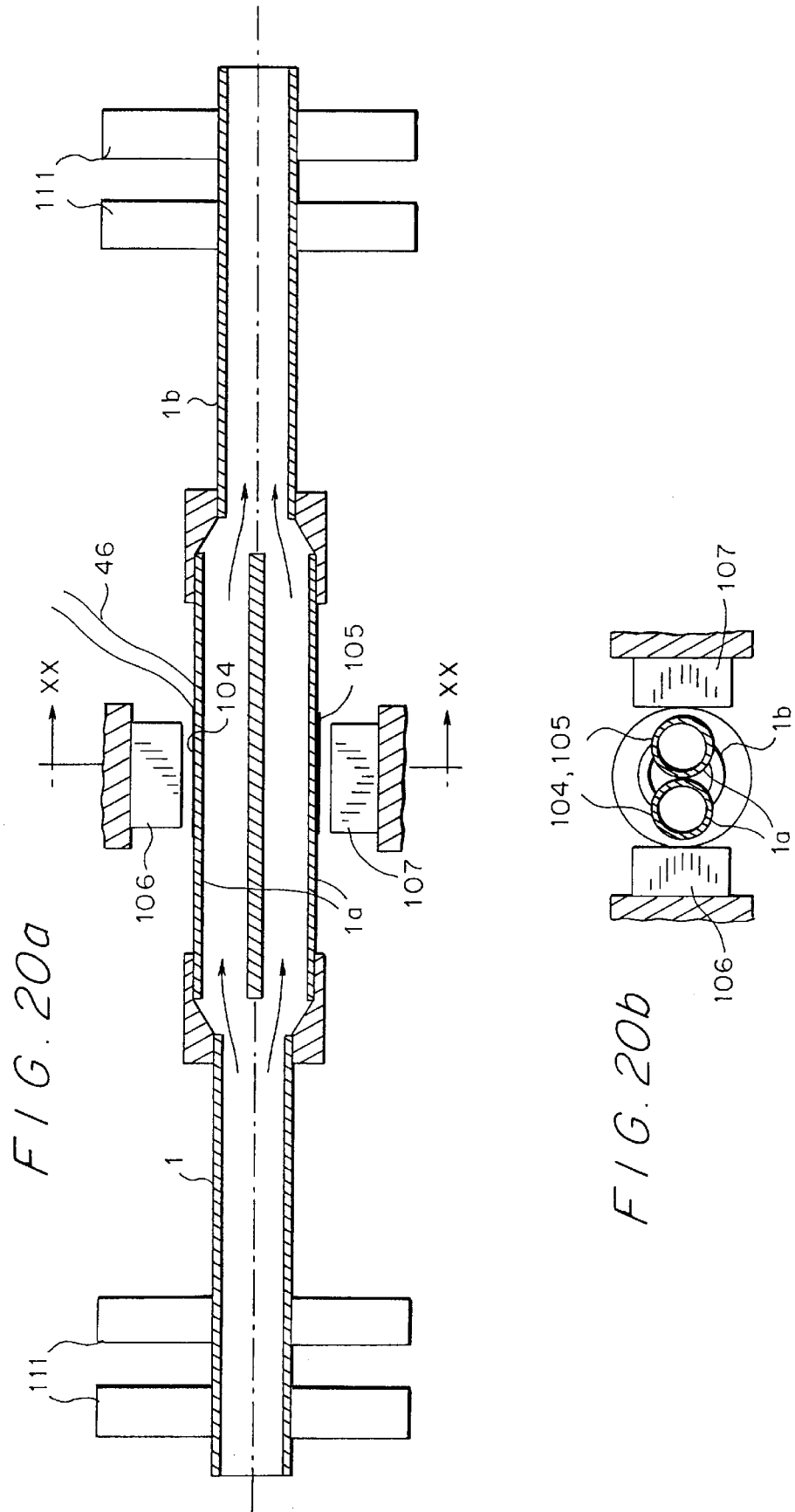

METHOD AND DEVICE FOR MEASURING THE CHARACTERISTICS OF AN OSCILLATING SYSTEM

DESCRIPTION

From "The Marconi Review", Vol. 43, Nr. 218, page 156 ff, a method and a device for measuring the characteristics of an oscillating system is known. Resonating sensors are described in R. M. Langdon, J. Phys., E: Sci. Instrum., Vol.18, 1985, p. 103–115 and in W. Göpel et al., Sensors, Verlag VCH, Weinheim, 1994. These three references are designated as integral parts of the present application. A mechanical oscillator is excited near its eigenfrequency with a first transducer at a stabilised frequency. Usually the response of the oscillator is measured with a second transducer. For example the damping of the oscillator can be obtained from the frequency difference generated by shifting the phase between two values in a phase-locked loop. One of the most important drawbacks of this procedure is the fact that cross-talk between the two transducers can hardly be avoided, especially when the oscillating system has small dimensions or if the measured signal is too weak.

EP-A-297 032 discloses a viscosimeter. It comprises a resonating system with a cylindrical torsional resonator. A piezoelectric excitation transducer is coupled to the resonator and is excited in the vicinity of a resonance frequency of the resonator with a sinusoidal signal. A measuring transducer measures the resulting vibration of the resonator. In a phase locked feedback loop between the two transducers the phase angle is shifted between two given values. From an evaluation of the resulting frequency shift the viscosity of a fluid surrounding the resonator is calculated.

In Patent Abstracts of Japan, vol. 10, no 48 (P-431) a vessel is torsionally elastically suspended. A coil is fixed to the vessel, the coil co-operating with permanent magnets. The coil is connected to two amplifiers via a change over switch. In a first stage the coil receives a pulse signal from the first amplifier to rotate the vessel. Then the switch is charged over and the resulting voltage output of the coil is amplified by the second amplifier. From the attenuation of this signal and from its wave form the blood clotting process is deducted.

The present invention proposes a method and a device for measuring the characteristics of an oscillating system. Such characteristics include the resonance frequencies and the corresponding damping coefficients of the oscillating system. One of the main features of the invention is that it solves the problem of cross-talk.

Thanks to the use of a gated alternate sensing and excitation scheme, cross-talk between two transducers can be completely avoided. Thus resonators (for example mechanical oscillators) can be built in very small sizes. Another advantage of the method is the fact that it allows the use of transducers that are prone to high cross-talk like electromagnetic transducers. Because the method proposed in this invention allows the construction of very small resonators, it can be used for example to build blood viscometers which are capable of measuring on-line (directly as it comes from the vein) or in-vivo (in the vein or artery) the viscosity of blood, or of any other body fluid since the volume necessary for the measurement is small (<1 cm$^3$). The direct measurement of the viscosity of blood without addition of anticoagulants would have for example a great significance as a diagnostic instrument capable of evaluating the action of certain drugs or of the health state of high risk patients. Another important application is the monitoring of blood viscosity in surgical operations (for example in heart-lung machines). The concept of a blood viscometer presented here can also be used for any other biological fluid. Such applications were not possible hitherto, because, amongst other reasons, till now, viscometers could not be built in sufficiently small sizes.

Another advantage of the method proposed in the present invention is the fact that the same single transducer can be used for both excitation and sensing. This simplifies the fabrication of the transducer and contributes also for example to the fact that mechanical oscillators can be built in small sizes. Another advantage is the simplification of the electronic circuitry for driving, sensing and evaluation. Furthermore, the measurement range of sensors, for which the damping is the prime quantity to be measured, e.g. viscometers, can be extended.

The method proposed in this invention can be applied to a great number of oscillating systems, in particular to mechanical resonator-sensors, for example to measure the density, the liquid level, the flow rate or the viscosity of fluids. Further advantageous applications are vibrating wire gauges, used for example as force sensors in balances, quartz force sensors, quartz pressure sensors and accelerometers, surface acoustic wave sensors, temperature sensors. Based on this method devices can be designed which are capable of measuring two or more of the above-mentioned quantities simultaneously, for example by combining measurements in more than one mode of vibration of the resonator. The method can also be applied to micro-structural resonators. Such micro-structural devices have typically sizes of a few $\mu$m and are fabricated, for example, using technologies developed for semiconductor manufacturing. Because of the small size of these sensors, the single transducer scheme is particularly important. The method is also applicable to resonators which are used in scanning tunneling microscopes and in atomic force microscopes.

Preferred embodiments of the basic concept of the invention will now be explained with reference to the following drawings. They show in FIG. 1 a circuit for gated driving and sensing, FIG. 2 time diagrams for a few signals during the operation of the circuit according to FIG. 1, FIG. 3 a phase-sensitive detector FIGS. 4a and 4b the input and output signals in the detector according to FIG. 3

Figure 5:
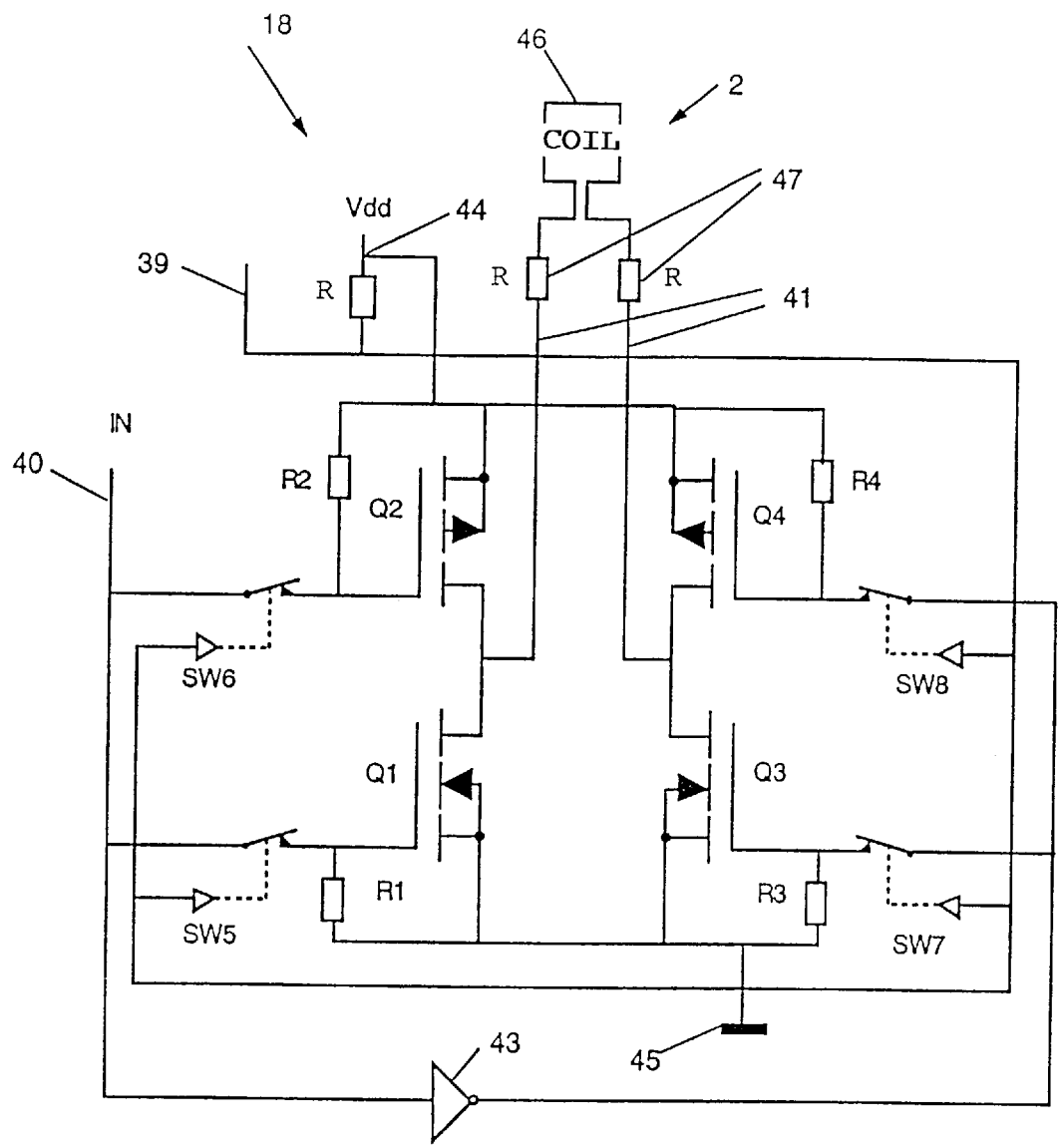

FIG. 5 a power amplifier

Figure 6:
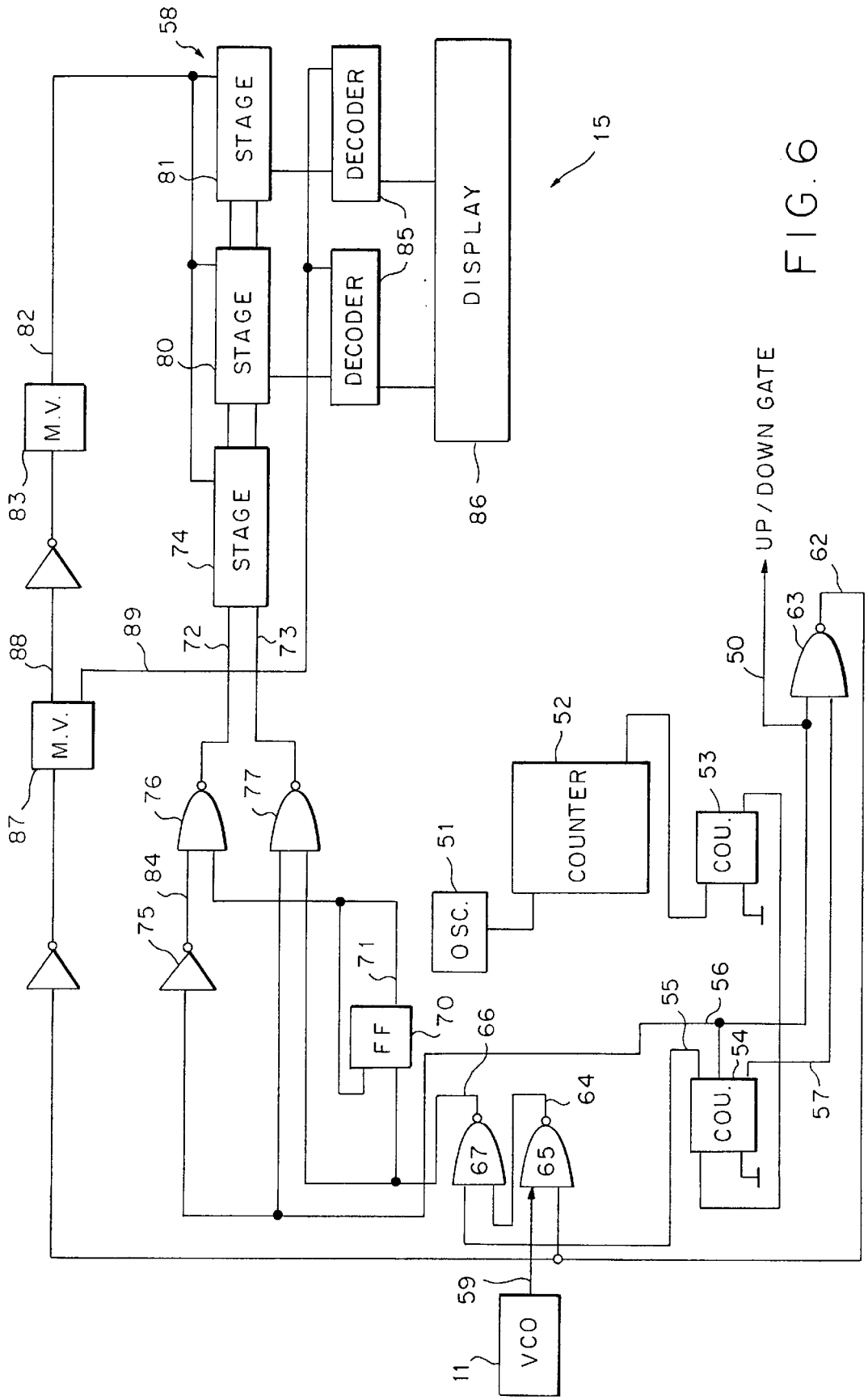

FIG. 6 a circuit for the evaluation

Figure 7:
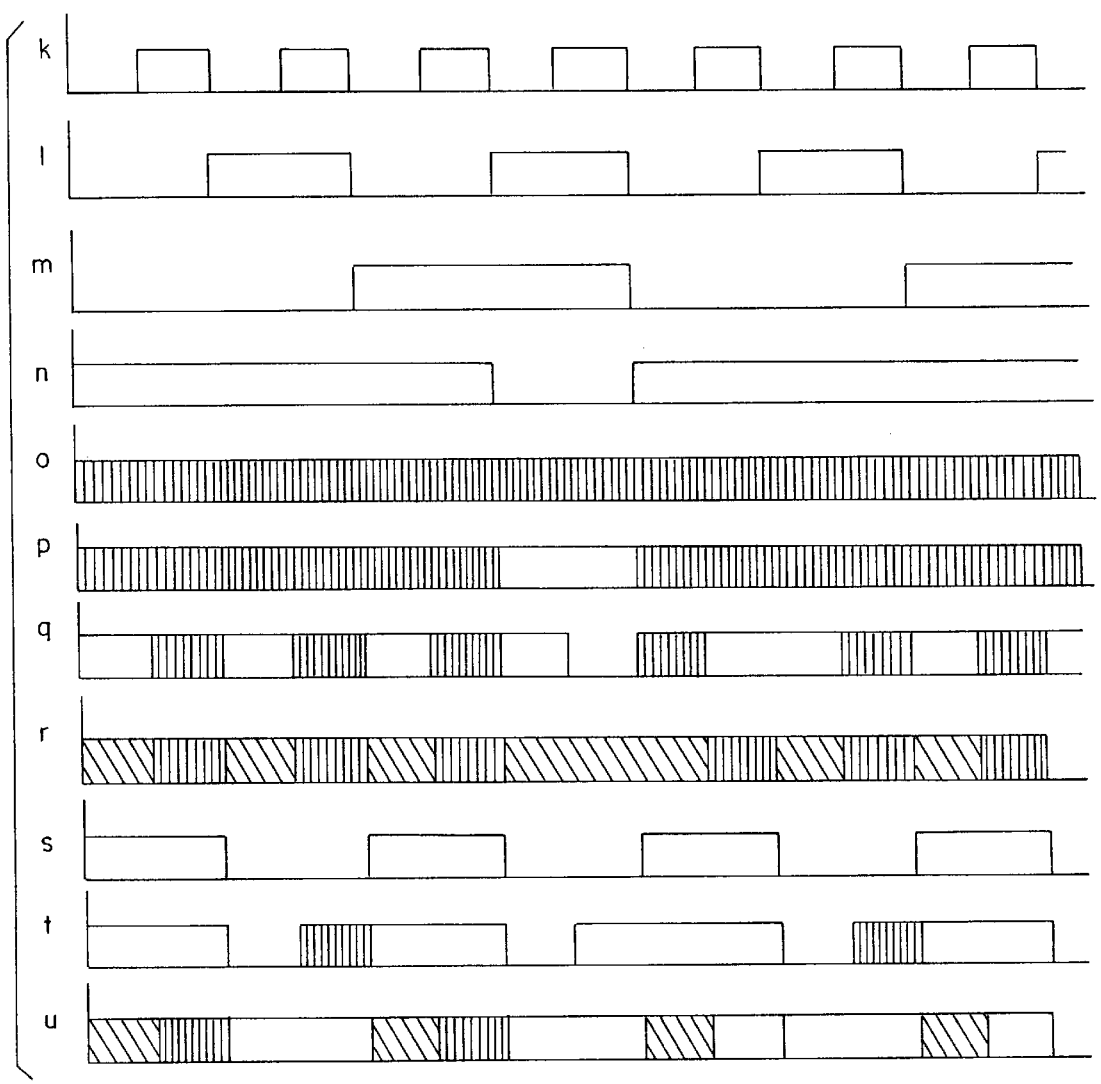

FIG. 7 time diagrams for a few signals in the circuit according to FIG. 6

Figure 8:
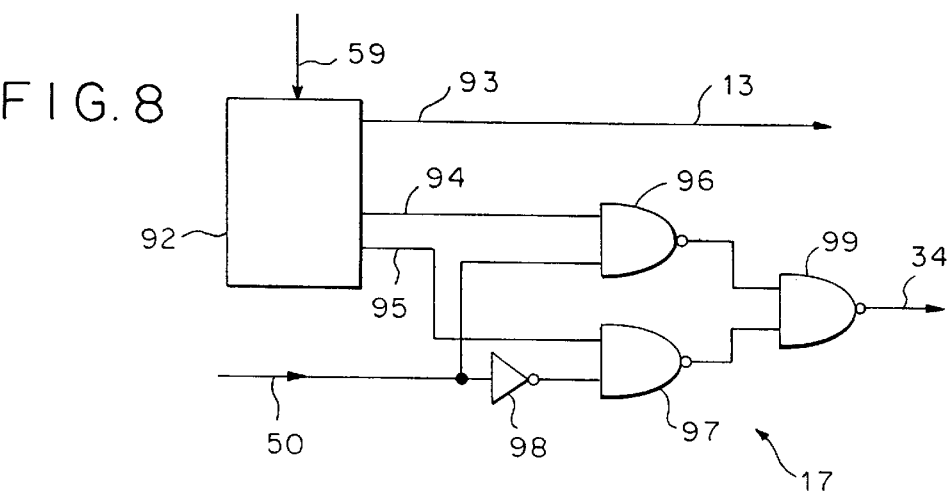

FIG. 8 a phase shifter

Figure 9:
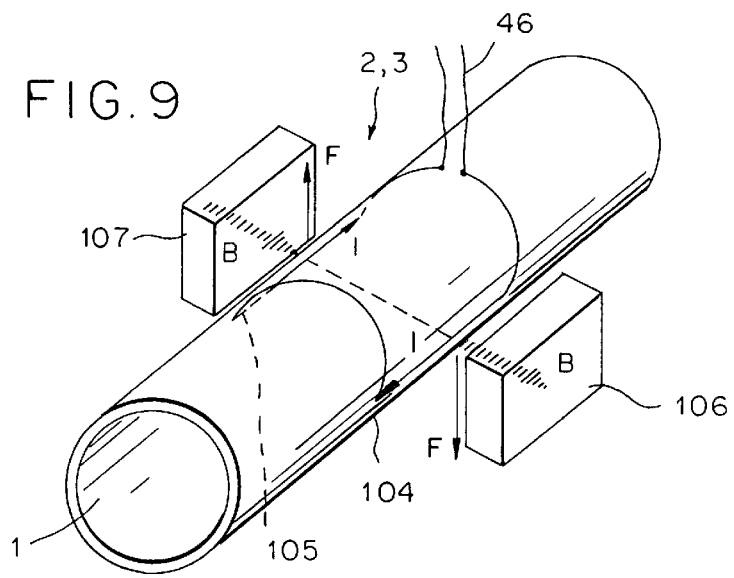
Figure 10:
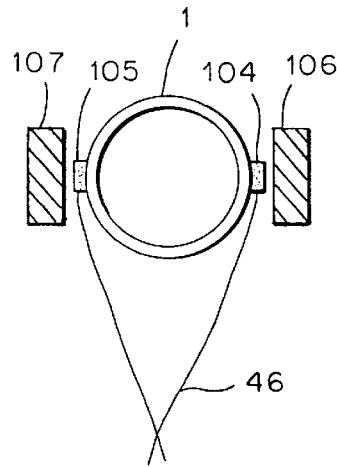

FIGS. 9 and 10 design sketches for the transducer set-up

Figure 11:
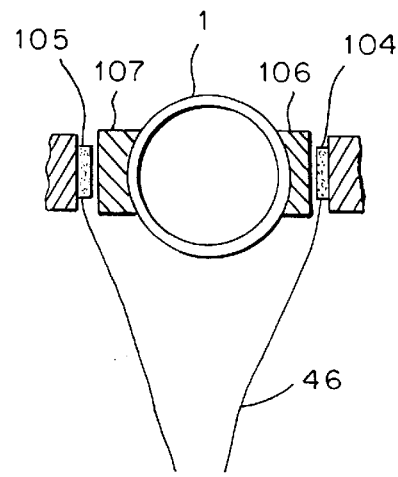

FIG. 11 an alternative to FIGS. 9 and 10

Figure 12:
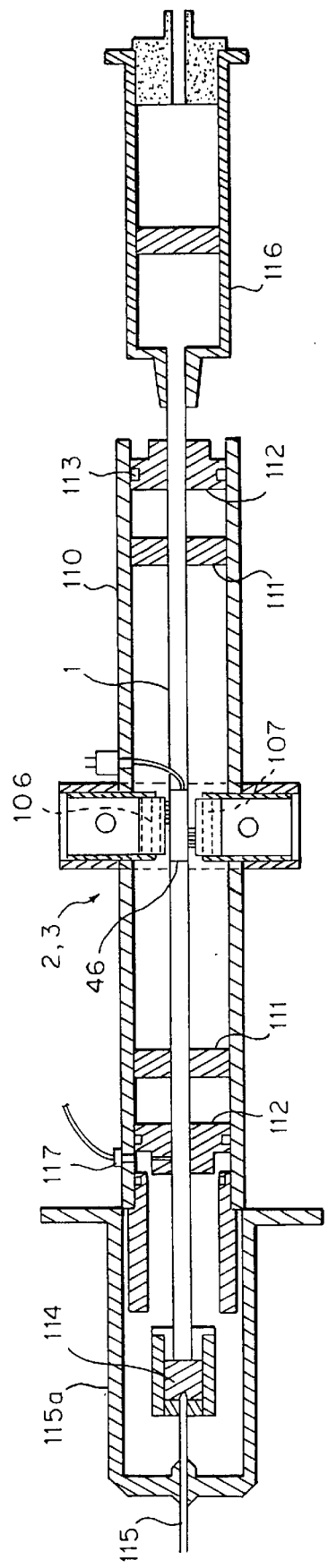

FIG. 12 an axial section through the embodiment of a viscometer for biological fluids FIG. 13 a resonator with transducer FIGS. 14 to 19 side and front views of three further resonators with transducers FIGS. 20a and 20b a resonator assembly to measure both density and viscosity of a fluid First the circuitry for exciting a mechanical resonator near its eigenfrequency and for measuring and evaluating the frequency and the phase-shifts will be described. The circuitry is suited to be used with any type of resonator (rod, tube, membrane, wire etc.), any type of transducers (piezoelectric, electromagnetic, etc.), any type of periodic driving signal (sinusoidal, rectangular, etc.). In the following, only the preferred embodiment combining excitation with rectangular pulses and electromagnetic transducers will be discussed.

Figure 2:
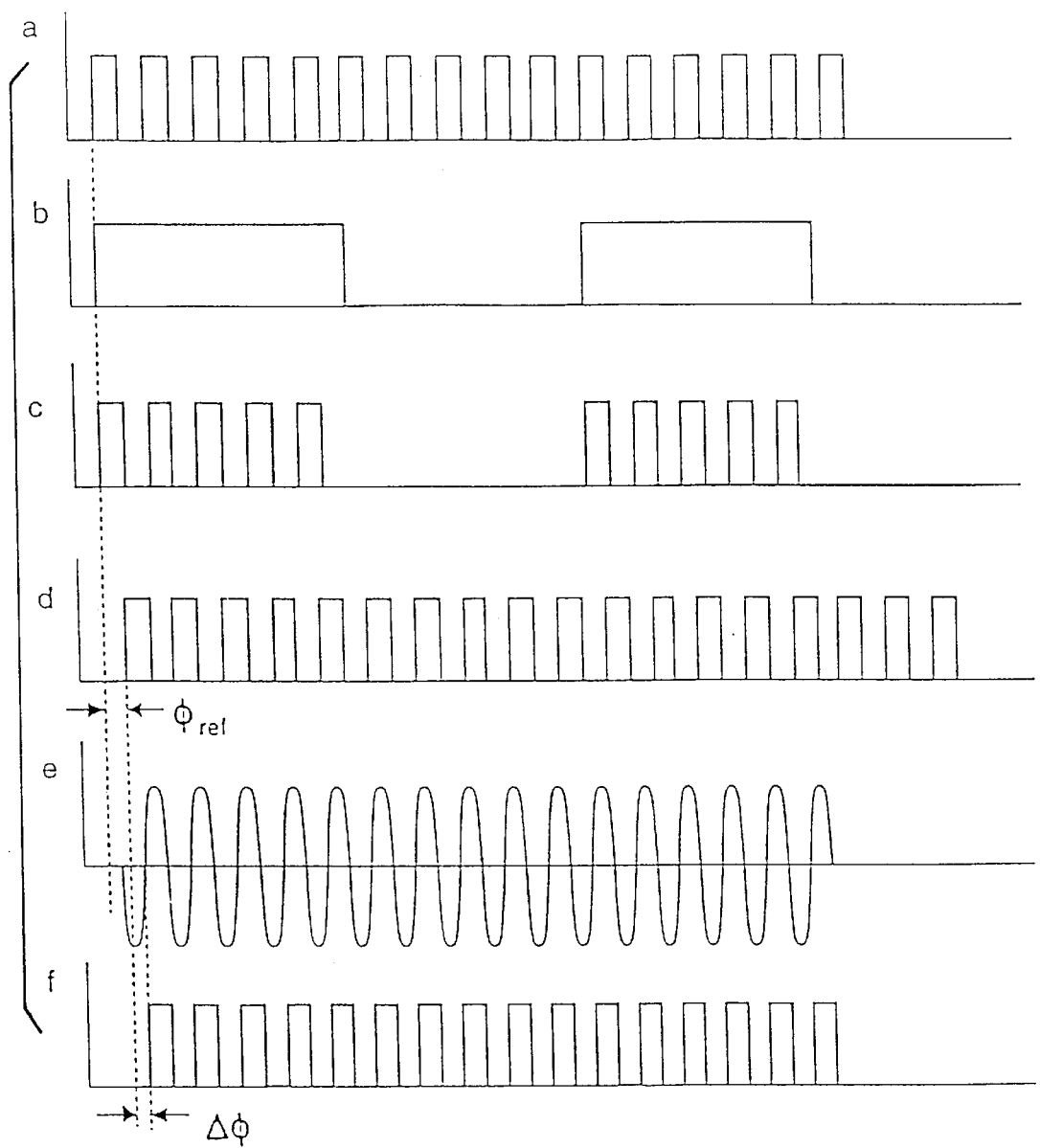

FIG. 1 shows the main features of a circuit driving the resonator 1 with a phase-locked loop and using gated alternate excitation and sensing. The time functions of the driving signal are periodic rectangular pulses. The resonator 1 has a driving transducer 2 and a sensing transducer 3. The circuit 10 has a voltage-controlled oscillator 11. The value of the output frequency of the oscillator 11 is for example 16 times the eigenfrequency of the resonator. The output 14 of the oscillator 11 goes on the one side to an evaluation and display device 15 and on the other side to a phase shifter 17. The phase shifter 17 has two outputs 13, 34 which oscillate synchronously with the eigenfrequency of the resonator 1. The time-function of the output 13 is shown in FIG. 2 as trace a. The output 34 is phase-shifted with respect to the output 13 by $\Phi_0 \pm \delta\Phi$. The quantity $\Phi_0$ corresponds to the phase required by resonance, whereas $\delta\Phi$ is the phase-shift introduced for the damping measurement. The output 13 is connected with the input of the synchronous gate 16 and with a switch and amplifier unit 18 which is indicated in FIG. 1 in simplified form.

The synchronous gate 16 is for example a 4-stage binary counter. The last stage gives the output 21. During eight cycles of the signal at the output 13 and in synchronous phase with it, the gate is turned on, and during eight further cycles it is turned off. The result is represented in trace b of FIG. 2, where for reasons of brevity only five cycles are shown. If the output 21 is turned on, the switch 19 is closed, so that the power amplifier 20 excites the driving transducer 2 synchronously with the output 21 (see FIG. 2, trace c), with rectangular pulses having the frequency of the output 13.

The output 21 controls with the help of an inverter 26 two further switches 27, 28, which are hence closed when the switch 19 is open. The signal of the sensing transducer 3 is amplified in a signal amplifier 29. Its output 30 is represented in trace e of FIG. 2. Another amplifier 31 whose one input is grounded, converts output 30 into a rectangular signal as output 32. This output 32 of the amplifier 31 is represented in FIG. 2 in trace f. In a phase-sensitive detector (PSD) 33 this output 32 is compared with the output 34 of the phase shifter 17 (traced in FIG. 2). Thus, from the phase shift between these two signals, a signal at the output 35 of the PSD 33 is created, whose DC (direct-current) value is proportional to the phase difference. When the switch 27 is turned on, the output 35 goes to the input of a control unit 36 which can be for example an integrator. The output 37 of the control unit 36 controls the frequency of the oscillator 11 so, that the output 35 has the value corresponding to the phase shift $\Phi_0 \pm \delta\Phi$ between the excitation and the response of the resonator. If the switch 27 is turned off, the output 37 remains constant. The control unit 36 therefore constitutes an integrate and hold circuit, the content of which is updated during time intervals in which the transducer 2 is not excited. That is, the frequency-control unit comprises memory means for controlling the vibration according to past vibrations.

In a way which will be explained further down, the unit 15 shifts the phase in the phase shifter 17 periodically between two values, for example between $\Phi_0 \pm 22.5°$ or between $\Phi_0 \pm 45°$. From the difference between the corresponding measured frequencies, the damping of the resonator 1 is then evaluated in the unit 15.

There is no possible cross-talk between the transducers 2 and 3, because the measurement needed to control the oscillator 11 is only carried out during the period when the driving transducer 2 is not driven.

The use of the same single transducer 2 or 3 for driving and sensing is also possible. This is indicated in FIG. 1 with the dashed line 38.

Figure 3:
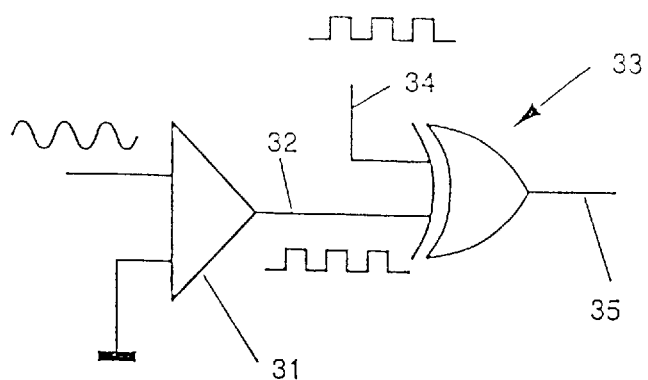
Figure 4A:
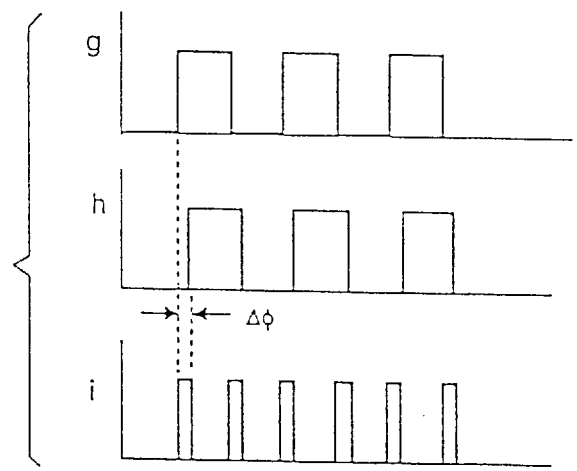
Figure 4B:
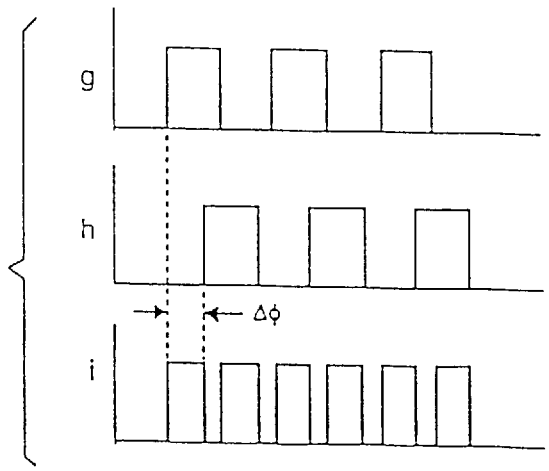

In FIG. 3 an embodiment of the PSD 33 in the form of an "exclusive OR gate" is depicted. In FIGS. 4a and 4b the time diagrams of the inputs 34(g) and 32(h) and the resultant output 35(i) are shown for two different values of the phase shift $\delta\Phi$. The output 35 of the PSD 33 is at logical 1 if one and only one of the inputs is turned on. The DC-value of this output 35 is proportional to the phase shift $\delta\Phi$ over the range from 0° (inputs in phase) to 180° (inputs 180° out of phase).

In the following, with reference to FIG. 5, a preferred embodiment of unit 18 especially suitable for the use of electromagnetic driving transducers 2 will be discussed. In a preferred embodiment of the electromagnetic driving transducer 2, driving currents in excess of 1 Ampere are not uncommon. This places quite high requirements on the characteristics of switch 19 represented symbolically in FIG. 1. dialogue switches which are free of distortion and yet pass large currents are difficult and expensive to produce. FIG. 5 shows an embodiment in which the combination of the power amplifier 20 and the switch 19 is represented by a power amplifier having a controllable output impedance. When input 39 which is connected with the output 21 of the synchronous gate 16 is supplied with a logical 0, the output impedance is raised to such a high value, that the driving transducer 2 is effectively isolated from the amplifier at output 41.

The circuit according to FIG. 5 is a full-bridge switching circuit utilising complementary power MOSFET transistors. The transistors Q1 and Q3 are N-channel enhancement mode power MOSFETs. Q2 and Q4 are P-channel enhancement mode power MOSFETs. The switches SW5 to SW8 are electronically controlled and all of their control inputs or gates are tied together on the common input 39. This input is connected to the output 21 of the synchronous gate 16. If this input 39 is supplied with a logical 1 all the switches SW5 to SW8 are closed. The control inputs of the MOSFET's Q1 and Q2 are connected with each other, also those of Q3 and Q4. A logical inverter 43 connected from the gates of Q1 and Q2 to the gates of Q3 and Q4 ensures that, when the gates of Q1 and Q2 are at ground, the gates of Q3 and Q4 are at the supply voltage $V_{dd}$, and vice versa. The input 40 is connected with the output 13 of the phase shifter 17.

During the driving phase the input 39 is at logical 1, hence turned on. Also, all the switches SW5 to SW8 are turned on. When now the input signal at input 40 which is connected with the output 13 of the phase shifter 17 is at logical 1, hence is turned on, then the gates of Q1 and Q2 are at $V_{dd}$. Q1 is turned on and Q2 is turned off. At the same time the gates of Q3 and Q4 are at ground, so that Q3 is turned off and Q4 is turned on. A current flows from the ground 45 through Q1, through the transducer coil 46, through the coil resistance 47 and through Q4 to the supply voltage $V_{dd}$. When the input 40 is at logical 0, the gates of Q1 and Q2 go to ground, so that Q1 is turned off and Q2 is turned on. At the same time the gates of Q3 and Q4 go to $V_{dd}$, so that Q3 is turned on whereas Q4 is turned off. Now the current path is reversed, going from ground through Q3, through the transducer coil 46 and through Q2 to $V_{dd}$.

When the input 39 is at logical 0, then all switches SW5 to SV8 are open. The gates of Q1 and Q3 are now connected through the resistances R1 and R3 with ground 45, hence Q1 and Q3 are turned off. The gates of Q2 and Q4 are connected through R2 and R4 to $V_{dd}$, hence Q2 and Q4 are also turned off. Since all four transistors are turned off, the coil 46 looks into an open circuit at the amplifier output 41. It is essentially disconnected from the power amplifier.

In FIG. 6 the unit 15 for evaluation and display is represented with more details together with the oscillator 11. The output 50 of this unit 15 switches the phase shift in the phase shifter 17 between two values $\Phi_0 \pm \delta\Phi$. The 1 MHz oscillator 51 provides the time base for counting and gating. Its output frequency is divided by the 14-stage counter 52, by the 4-stage counter 53 and further by the 4-stage counter 54. The counter 54 has three outputs 55, 56, 57. A First output 55 after the first counting stage subdivides the measurement cycle in two. In a first half, the pulses at the output 14 of the oscillator 11 are not counted until the frequency reaches a stable value; in the second half of the cycle the pulses at the output 14 are counted. The second output 56 with half the frequency of output 55 goes to output 50 for the switching of the phase shifter 17 between the two values $\Phi_0 \pm \delta\Phi$. The third output 57 is for switching to temperature compensation. The frequency of output 56 is typically in the range of seconds, while the driving frequency at output 13 is for example 10 kHz.

A phase-shift of ±45° corresponds for 10 kHz driving frequency and low damping to a frequency difference of only a few Hz, hence to less then one thousandth of the driving frequency. To obtain the required accuracy, a multiple of the driving frequency is counted. This multiple can be chosen such that, depending on the damping (i.e. viscosity of the fluid) the frequency difference is within the range of a three-stage decimal counter 58. In this fashion a good resolution for the frequency difference can be realised. The parameters are so adjusted, that the intrinsic damping of the resonator 1 gives a count difference greater than 10, so that the displayed count is greater than 1. Because of gating uncertainties in the phase shifting (the time of gating is not synchronised with the frequency of the oscillator 11), the smallest decimal is not displayed.

A temperature change in the resonator can produce frequency shifts over a measurement period which are comparable to the frequency difference corresponding to the damping. Therefore the unit 15 has a temperature compensation algorithm. In the following it will be assumed that if output 50 is at logical 1, the phase in the phase shifter 17 will be shifted in the positive direction and hence the frequency of the oscillator will be increased.

The counting will be performed over three half-cycles of the output 50. In the first half cycle, when the output 50 is at zero, the up-down counter 58 counts down, but it counts only half of the pulses of the oscillator 11 at the input 59. In the second half cycle the output 50 is at logical 1 and the counter 58 counts up, but now it counts the full frequency of the input 59. In the third half period it counts again down half the frequency. Hence from the upper frequency in the middle of the cycle the average of the lower frequencies at the beginning and at the end of the cycle is subtracted. Thus the linear component of the frequency drift due to temperature is compensated exactly.

In the diagram of FIG. 7 the trace k is the oscillation at output 55, trace l is the one at output 56 and trace m corresponds to output 57 of the counter 54. The oscillation after the gating of the phase shifter 17 has to be stabilised before the counting of the frequency begins. The trace l is the output 50 and shows when the counter 58 counts up or down. Trace m represents the temperature compensation cycle at output 57. Trace n is the output 62 of NAND 63, which has both outputs 56, 57 as input. Trace o is the strongly scaled version of the frequency of the oscillator 11 at input 59 to be counted. Trace p shows the output 64 of NAND 65 whose inputs are connected with the outputs 59, 62 of the oscillator 11 and of NAND 63. Trace q is the output 66 of a NAND 67 whose inputs are the outputs 55 and 64. This signal 66 is applied to the reset input of a flip-flop 70 whose output is shown as trace r in FIG. 7. When the frequency of the oscillator 11 is applied to the reset input of the FF 70, the output 71 gates with half of this frequency. When the reset input of FF 70 is constant, the output 71 is undetermined. In trace r of FIG. 7 this is indicated with diagonally hatched areas. Outputs 56 and 66 are the inputs of NAND 77. Output 71 and output 56 through an inverter 75 are the inputs to NAND 76. Outputs 72 and 73 of NAND's 76 and 77 are the inputs of counter 58.

The counter 58 is a three-stage, binary coded decimal up-down counter. When the input 73 is at logical 1 and impulses are supplied to the input 72, the counter 58 counts up. However, when the input 72 is at logical 1 and impulses are supplied to the input 73, the counter 58 counts down. All the stages 74, 80 and 81 of the counter 58 are reset by a signal at output 82 of a one-shot multivibrator 83.

Up- or down- counting is therefore controlled by supplying the proper input 72,73 of counter 58, while keeping the other input at logical 1. This is produced by NANDs 67,76,77 and inverter 75. Trace s in FIG. 7 is the output 84 of inverter 75 and trace t the input 73. Trace u shows the input 72. During each phase of up or down counting one of the inputs of counter 74 is active, while the other is at logical 1.

Thereby, during three cycles of output 55 up-counting at a positive-phase-shift is performed at the full frequency of the oscillator 11, while down-counting at the negative phase-shift is performed in the first and third cycle of output 55 with half the frequency of oscillator 11. Furthernmore, the measurement interval can even be shortened by using several counting devices in parallel.

The outputs of the counters 80 and 81 contain a parallel representation of the instantaneous count. Display decoder/drivers 85 interpret this data for display by a 2-digit LED display 86. The display drivers must be latched during counting operations, and must be loaded with new data at the end of a counting cycle. Trace n in FIG. 7 shows output 62 of NAND-gate 63 . This output 62 goes to logical 0 for the fourth (non counting) cycle of the output 55 of the counter 54. On its low transition, one-shot multivibrator 87 is triggered. Its noninverted output 89 goes momentarily to logical 0, which serves to latch the count data in display decoder/drivers 85. The inverted output 88 of multivibrator 87 triggers a second one-shot multivibrator 83, whose output resets the three stages 74, 80 and 81 of the counter 58. The circuit is ready for another measurement.

In FIG. 8, the phase-shifter 17 is represented schematically. The input 59, which corresponds to the output 14 of the oscillator 11, is connected to an 8 stage binary ring counter 92. Its eight outputs are square signals with a frequency of $\frac{1}{16}$ of the frequency of input 59 and with a phase-shift of 22.5° with respect to each other. The output 93 of the first stage of the counter 92 is the excitation signal 13. Two further outputs 94 and 95 are phase-shifted with respect to the output 93 by 90°±α, respectively. α takes a value of 22.5° or 45°. They are connected to the input of two NAND gates 96, 97. The output 50 of the unit 15 is connected to the second input of NAND 96 and through an inverter 98 to the second input of NAND 97. The outputs of the NAND gates 96 and 97 are inputs to NAND 99, which is the output 34 of the phase-shifter 17.

When output 50 of the unit 15 is at logical 1, NAND 96 switches synchronously with output 94 and NAND 97 is switched on. The output 34 is phase-shifted with respect to output 13 by e.g. 45°. When output 50 is at logical 0, then NAND 97 oscillates and the output 34 is phase-shifted with respect to output 13 by 135°.

As an application of the method and arrangement according to the present invention a special torsional resonator will be described.

FIGS. 9 and 10 show the basic principle of the application of an electro-magnetic transducer. The resonator 1 is a tube. A coil 46 is rigidly attached to its outer surface in such a way, that two straight branches of wire 104 and 105 are parallel to the axis of the tube 11 and lie in a plane containing the axis. For clarity, the coil 46 is drawn with only one wire, however, several wires are also possible. This transducer set-up can be used for both excitation and detection of the mechanical vibration.

Close to the wires 104 and 105, permanent magnets 106 and 107 are attached to the housing of the tube. The field lines B of the magnets 106 and 107 have the same direction, are parallel to the common plane of the wires 104 and 105 and orthogonal to the axis of the tube 1. If an electrical current I flows through the coil 46, the currents in the wires 104 and 105 have opposite direction. Therefore, the magnetic field B produces a force couple, which is statically equivalent to a torque about the axis of tube 1. If an alternating current is used, torsional vibrations about the axis are produced in the tube 1. These vibrations correspond to a resonance of tube 1, if the current alternates with a frequency given by the resonance frequency of tube 1.

Instead of using permanent magnets 106 and 107, DC powered electromagnets might be used as an alternative.

If the transducer 2, 3 is used for the measurement, the magnetic field B induces a voltage in coil 46, which is proportional to the angular velocity of tube 1. If the resonator 1 vibrates close to its eigenfrequency, the voltage is sinusoidal in shape with an amplitude proportional to the amplitude of vibration.

The transducer 2,3 is particularly well suited to the excitation and measurement of vibrations in a resonator, whose surface is vibrating parallel to itself, e.g. in a torsional resonator. The electromagnetic coupling between the fixed part and the moving part of the transducer is weak. Therefore, the contribution of the transducers to the intrinsic damping of the resonator will be negligible.

If a transducer for driving and another one for sensing need to be attached to the resonator 1, the wires 104 and 105 can be arranged either in a common plane, or in two planes which are orthogonal to each other. In the latter case, electrical cross-talk between excitation and measurement is minimised. The two coils 46 of measurement and excitation can also be arranged on top of each other. Thereby, only a single pair of magnets is needed.

In FIG. 11, an alternative to the arrangement in FIGS. 9 and 10 is shown. The coil 46 is rigidly attached to the housing, while the two magnets 106,107 are mounted on the tube 1. The functional principle is the same.

As an other alternative, electromagnetic acoustic transducers (EMATS) might be used for driving and/or sensing. Such transducers are described e.g. in a publication by R. B. Thompson, IEEE Transactions on Sonics and Ultrasonics, Vol. SU-20, No 4., 1973, p. 340–346.

The method and device described above has many scientifically and industrially relevant applications, one of which is particularly important: The on-line or in-vivo measurement of the viscosity of blood or other biological fluids.

"On-line" means in this context continuous measurement of the viscosity of the blood taken directly from the blood vessels via a hypodermic needle, without the addition of anticoagulant agents to the blood fluid. "In-vivo" means continuous measurement of the viscosity of the blood by introducing the mechanical resonator, which we shall call the probe, directly into the blood vessels. The viscosity might also be continuously monitored during surgery, while blood is being pumped through a tube-like sensor.

In FIG. 12 an on-line measurement probe is shown. The resonator 1 is a long thin-walled tube. A coil 46 as shown in FIG. 9 is attached to the tube 1, for example at its middle. The magnets 106 and 107 are rigidly mounted to the tubular housing 110. Two inertial disks 111 are rigidly attached to the tube 1 at equal distances from transducers 2, 3, and two further disks 112 are attached at a certain distance from the inertial disks 111 on both sides. The disks 111 are not touching the housing 110, whereas the two disks 112 are connected elastically to the housing by means of two O-rings 113. The 4 disks 111 and 112 have the purpose of vibration isolation. Thus the influence of the housing 110 and the surroundings on the intrinsic damping of the resonator 1 is minimised. The inertial disks 111 enforce nodes of the vibrational mode at their position. The eigenfrequency of the resonator is preferentially kept in the kHz range. In particular a mode can be chosen, which has a displacement maximum in the middle.

Alternatively, higher modes of vibration might also be used, then the transducers 2, 3 are again preferably attached to the tube I near a maximum of the vibrational amplitude of the mode desired.

At one end, a hypodermic needle 115 is attached via a flow diffusor 114 to the tube 1. The other end of tube 1 is connected to a syringe or a container 116 with partial vacuum. The diffusor 114 prevents bubbles from being formed when the blood is drawn into the tube 1. In addition, a temperature sensor 117 may be built into tube 1. To perform a measurement, first the needle 115 attached to the cylinder 115a is introduced into a vein of the subject. Then the rest of the assembly illustrated in FIG. 12 is introduced into the cylinder 115a, while the flow diffusor 114 is being perforated by the other end of the needle 115. The blood is then drawn through tube 1 into the container 116, while the damping of the resonator is being measured. From the damping the viscosity is determined.

Figure 13:
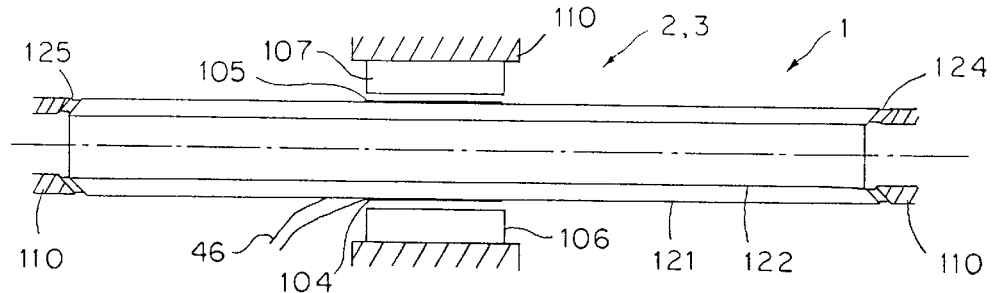

In FIG. 13, a special version of the resonator 1 is shown, which is particularly short and therefore particularly useful for the in-vivo measurement of blood viscosity. In this configuration the resonator 1 consists of two tubes 121 and 122. The tube 122 is located inside the tube 121 without touching it except at the ends. At these ends the tubes have a rigid and airtight connection with each other, produced e.g. by laser welding or brazing. The space 123 between the tubes 121, 122 is preferably evacuated to minimize the intrinsic damping of the resonator 1.

In the embodiment shown in FIG. 13, the inner tube 122 vibrates with a phase shift of 180° with respect to the vibration of the outer tube 121. The two ends 124,125 are nodes of the torsional vibration at one of its eigenfrequencies in the resonator 1. Therefore no additional inertial masses are needed for the vibration isolation. The two ends 124 and 125 can be centered directly within the housing 110, e.g. by means of O-rings 124. Therefore, the embodiment of FIG. 13 can be built to be as small as possible.

Figure 14:
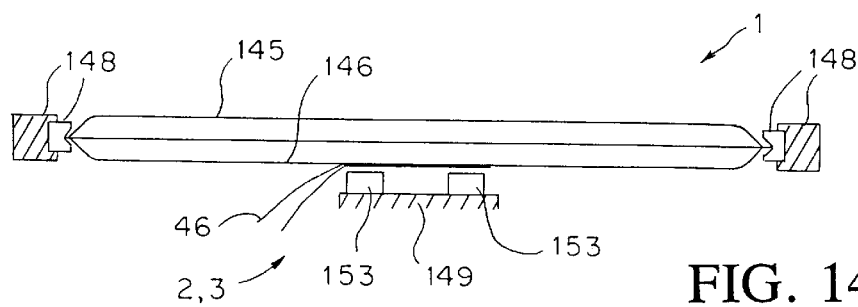
Figure 15:
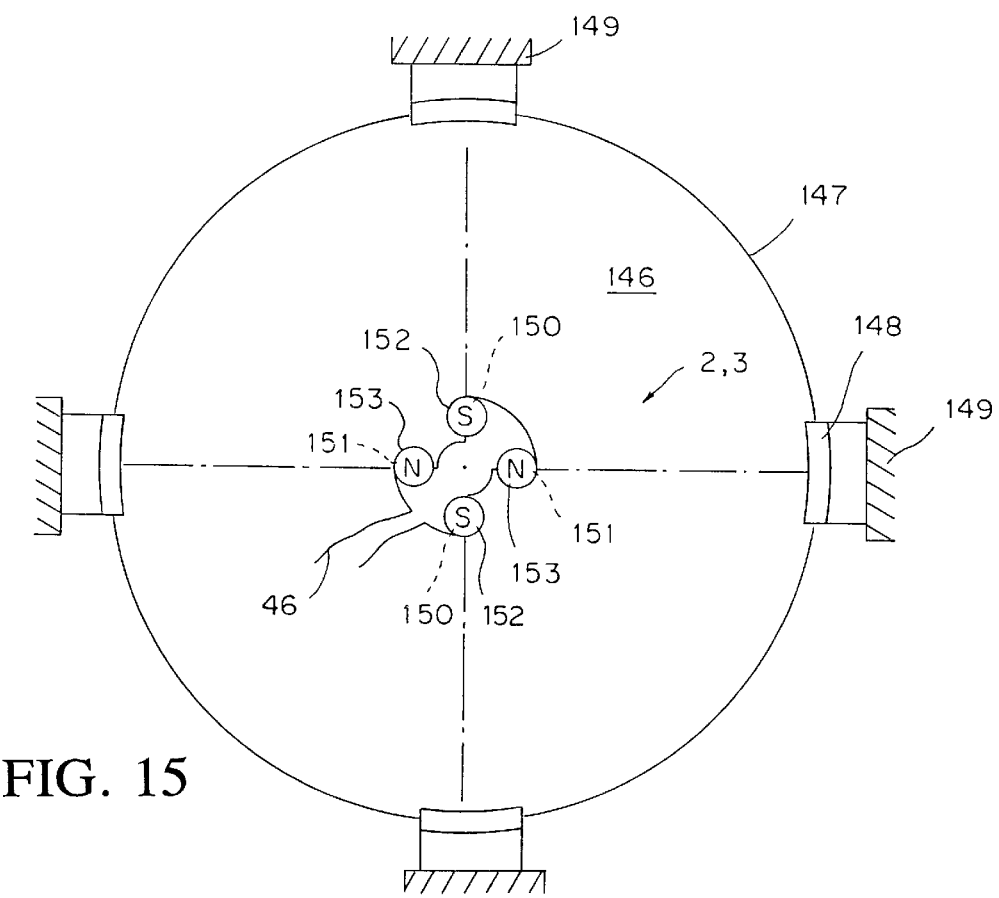

In FIGS. 14 and 15, another embodiment of the resonator 1 is shown. It consists of two flat, circular membranes 145, 146 which are arranged symmetrically and without touching on top of each other. They are rigidly connected along their edges 147 e.g. by welding or brazing. They are held in a housing 149 by several rubber blocks 148, which are distributed along the circumference of the membranes 145, 146. A coil 46 of transducers 2, 3 is attached to the membrane 146. The coil 46 has 4 radial branches of wire 150, 151 spaced at equal angles. When the current flows from the centre to the edge in the two opposite branches 150 of coil 46, the it flows from the edge to the centre in branches 151 and vice versa. Below the branches 150 and 151, four permanent magnets 152 and 153 are attached to the housing 149. The magnetic fields of the magnets 152, 153 are perpendicular to the plane of the membranes 145, 146. The polarization for magnets 152 is opposite the one of magnets 153. If an alternating current with a frequency corresponding to one of the torsional eigenfrequencies of the membranes 145, 146 is applied to coil 46, the two membranes vibrate with a phase difference of 180°. The edge 147 is a nodal line, thereby the rubber blocks 148 do not influence the damping of the vibration. A thin layer of fluid might be applied to the upper membrane in order to measure its viscosity.

Alternatively, the transducer 2, 3 in FIGS. 14, 15 can be designed in such a way, that the membranes vibrate perpendicular to their surface. Then the resonator 1 can be used to determine the mass of the material lying on the membrane 145.

Figure 16:
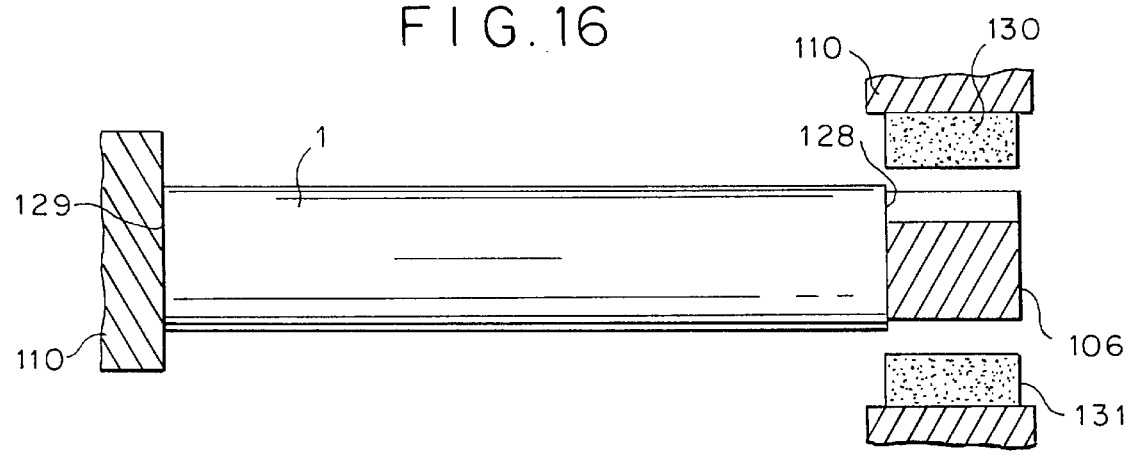
Figure 17:
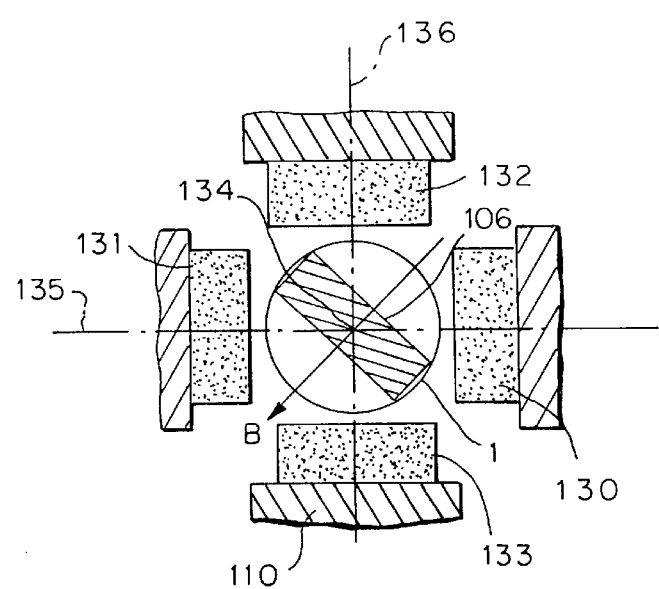

In FIGS. 16 and 17 a further version of transducers 2, 3 is shown. Here the transducer is located at the end face 128 of a circular cylindrical resonator 1. The other end 129 of resonator 1 is clamped, preferably by means of inertial disks (not shown in FIG. 12). A permanent magnet 106 having a magnetic field B which is perpendicular to the axis of the resonator 1 is rigidly attached to the end 128. Four coils 130 to 133 are distributed at equal angles around the magnet 106 and have equal distance from the axis 134 of the resonator 1. the axes 135, 136 of coils 130 to 133 are orthogonal to the axis of the resonator 1 and at an angle of 45° with respect to the magnetic field B. Two opposite coils 130, 131 are connected in series or in parallel to act as the driving transducer 2 together with the magnet 106, whereas the remaining two coils 132, 133 together with magnet 106 make up the sensing transducer 3.

This transducer design has extremely low electromagnetic cross-talk between driving and sensing transducers 2, 3 because the voltage induced in the measurement coils 132, 133 by the driving coils 130, 131 cancel out. Alternatively, all coils 130 to 133 can be connected in parallel or in series to act as driving transducer 2 or sensing transducer 3 or both.

Figure 18:
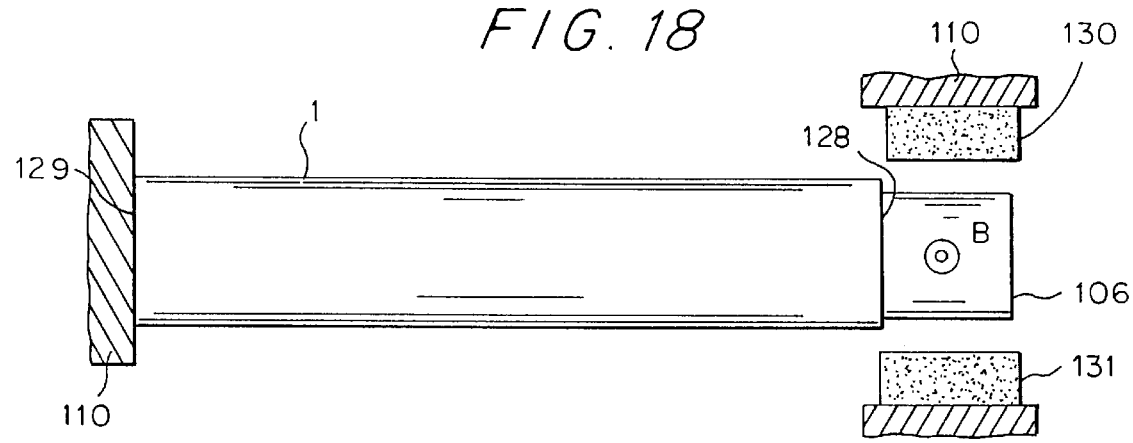
Figure 19:
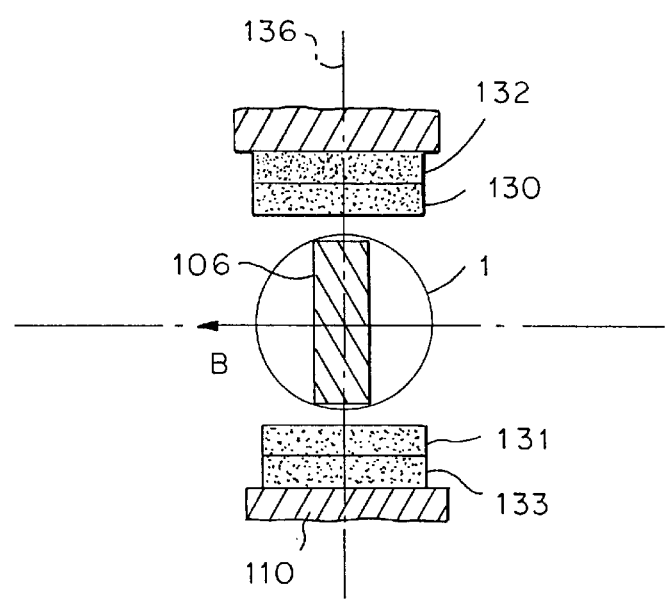

In FIGS. 18 and 19, two further designs of the embodiment according to FIGS. 16 and 17 are shown. Corresponding parts have the same designations, hence the explanation follows the one given for FIGS. 16 and 17.

In the version of FIG. 18 only two coils 130 and 131 are used and the magnetic field B of the permanent magnet 106 is perpendicular to the axes 136 of the coils 130, 131 and the axis of the resonator 1. For example, the coil 130 can be used for driving and the coil 131 for sensing, or coils 130 and 131 can be connected in series or in parallel and alternately used for driving and sensing.

The version of FIG. 19 is the same as FIG. 18, except that the four coils 130 to 133 are attached to the housing 110.

In the embodiment of FIG. 20 a special version of the resonator 1 is shown, which consists of two tubes 1$a$ arranged in parallel, which are rigidly and symmetrically connected to two further tubes 1, 1$b$ at both ends of the two tubes 1$a$. The two tubes 1 and 1$b$ have the same axis of symmetry. The resonator 1, 1$a$, 1$b$ vibrates as a whole in a torsional mode, whereby the middle part 1$a$ carries out a rotation about the common axis of the tubes 1, 1$b$. The vibration of the tube assembly 1, 1$a$, 1$b$ is isolated from the environment by means of the inertial masses 111.

The fluid flowing in tube 1 is divided into the tubes 1$a$ and joined together again in tube 1$b$. The transducers 2,3 described above and shown in FIG. 9, 10 or 11 are used to drive and sense the vibration. This assembly allows the simultaneous measurement of the viscosity and the density of a fluid by measuring its resonance frequency and mechanical damping.

The viscometer in the shape according to FIGS. 12 and 13 and the embodiment of FIG. 20 applied to the combined measurement of density and viscosity can also be used together with other ways to measure the characteristics of a vibrating system, in particular ways described in the references mentioned at the beginning of the description of the present invention.

What is claimed is:

1. A method to measure the characteristics of a vibrating system in a vicinity of a resonance frequency of a resonator, said method comprising the steps of:

providing a measuring device including said resonator (1), said measuring device further comprising
   a transducer (2,3) coupled to said resonator and
   a feedback loop to stabilize a vibration of said resonator in the vicinity of said resonance frequency, said feedback loop comprising a switch (19,27,28), an oscillator (11), a frequency-control unit (36) further comprising a an integrator, and a gate generator (16) acting on said switch;

exciting said transducer by said oscillator during a finite first time interval, said first time interval including a number of cycles of the vibration of said resonator;

during said first time interval, interrupting the feedback loop between said transducer to said frequency-control unit by opening said switch;

measuring said vibration by said transducer during a second time interval, said second time interval not overlapping said first time interval;

updating said frequency-control unit during said second time interval; whereby said frequency-control unit controls said oscillator.

2. The method according to claim 1, wherein the step of providing said feedback loop further comprises providing the feedback loop with a phase shifter (17), and a phase sensitive detector (33), and wherein the method comprises the step of stabilizing said resonator by means of said phase shifter at two different phase values in the vicinity of said resonance frequency.

3. The method according to claim 2, comprising the steps of:

providing the measuring device with an up-down counter;

alternately setting the phase shift by said phase shifter to two different values $\Phi_0 \pm \delta\Phi$ between said counting intervals; and measuring frequency with the counter.

4. The method according to claim 3, wherein the counter is an up-down counter and comprising temperature-compensating steps of:

counting oscillations of said oscillator with said up-down counter during three counting intervals, said counting being in one direction during a first and a third of said counting intervals and in an opposite direction during a second of said counting intervals.

5. The method according to claim 1, including producing produces square pulses with said oscillator to excite said vibration periodically in said resonator by said transducer and said first switch.

6. The method according to claim 1, including a step of providing two transducers including a first exciting transducer (2) to excite the vibrations and a second measuring transducer (3) to measure the vibrations.

7. The method according to claim 1, wherein the integrator comprises an integrate and hold-circuit.

8. A device for measuring the characteristics of a vibrating system, the device comprising:

a resonator;

a transducer coupled to said resonator;

a phase-locked feedback loop comprising an oscillator, a phase shifter, a phase sensitive detector, a frequency-control unit, said oscillator being controlled by said frequency-control unit, said feedback loop further comprising at least one switch to alternately connect said transducer with an output of said oscillator and said transducer with an input of said frequency-control unit.

9. The device according to claim 8, wherein said resonator is a mechanical resonator.

10. The device according to claim 8, wherein the resonator is a torsional resonator.

11. The device according to claim 8, wherein said transducer is an electromagnetic transducers, comprising a permanent magnet attached to a first element and a coil attached to a second element vibrating relative to said first element.

12. The device according to claim 8, including a first exciting transducer to excite the vibrations and a second measuring transducer to measure the vibrations.

13. The device according to claim 8, wherein said transducer is attached to an outer surface of the resonator, said resonator having the shape of a tube, and wherein one end of said tube is connected to means to extract body fluids, the other end of said tube being connected to means to draw said body fluids through said tube.

14. The device according to claim 8, wherein a moving part of said transducer is attached to one of two coupled resonators, which vibrate with opposite phase and have similar eigenfrequencies and wherein the two resonators are spaced apart and mechanically connected at a node of the vibration.

15. The device according to claim 8, wherein said transducer is an electromagnetic transducer to excite and measure mechanical vibrations of the resonator, comprising a housing to protect said electromagnetic transducer, said transducer comprising a magnet attached to said resonator, said magnet being arranged so that its magnetic field is orthogonal to an axis of symmetry of said resonator, four coils attached to said housing, the axis of said coils being orthogonal to said axis of symmetry and at angles of ±45° to said magnetic field.

16. The device according to claim 8 for the measurement of the density and viscosity of a fluid, the resonator comprising two first tubes arranged in parallel, two second tubes rigidly attached to said first tubes at both ends, said second tubes having the same axis of symmetry, said four tubes containing said fluid, further comprising at least one transducer attached to said resonator, said transducer being connected to electronic means to measure the resonance frequency and the damping of said resonator and to compute the density and the viscosity of said fluid from said resonance frequency and said damping.

17. A viscometer for the measurement of the viscosity of body fluids directly during the extraction of said body fluids from the body, comprising a device according to claim 8, a tube, said tube being said resonator or being coupled to a second resonator, at least one transducer attached to said resonator, one end of said tube having means to extract said body fluids from said body, the other end of said tube having means to draw said body fluids through said tube, said transducer being connected to electronic means to measure the damping of said resonator and to evaluate the viscosity of said body fluids.

* * * * *